US010572959B2

(12) United States Patent
Verstandig et al.

(10) Patent No.: US 10,572,959 B2
(45) Date of Patent: Feb. 25, 2020

(54) SYSTEMS AND METHODS FOR A HEALTH-RELATED SURVEY USING PICTOGRAM ANSWERS

(75) Inventors: Grant Verstandig, Arlington, VA (US); Alexander Siedlecki, Washington, DC (US)

(73) Assignee: Audax Health Solutions, LLC, Washington, DC (US)

( * ) Notice: Subject to any disclaimer, the term of this patent is extended or adjusted under 35 U.S.C. 154(b) by 1149 days.

(21) Appl. No.: 13/310,373

(22) Filed: Dec. 2, 2011

(65) Prior Publication Data
US 2013/0046552 A1    Feb. 21, 2013

Related U.S. Application Data

(60) Provisional application No. 61/524,915, filed on Aug. 18, 2011.

(51) Int. Cl.
*G06Q 10/00* (2012.01)
*G06Q 50/22* (2018.01)
*G06Q 30/02* (2012.01)
*G16H 10/20* (2018.01)

(52) U.S. Cl.
CPC .......... *G06Q 50/22* (2013.01); *G06Q 30/02* (2013.01); *G16H 10/20* (2018.01)

(58) Field of Classification Search
CPC .............................................. G06Q 50/22–24
USPC ........................................................ 705/2–3
See application file for complete search history.

(56) References Cited

U.S. PATENT DOCUMENTS

| | | | |
|---|---|---|---|
| 6,039,688 A | 3/2000 | Douglas et al. |
| 6,339,410 B1 | 1/2002 | Milner et al. |
| 6,368,273 B1 | 4/2002 | Brown |
| 6,454,705 B1 | 9/2002 | Cosentino et al. |
| 6,849,045 B2 | 2/2005 | Iliff |
| 7,357,639 B2 | 4/2008 | Stillman |
| 7,379,867 B2 | 5/2008 | Chelba et al. |
| 7,603,282 B2 | 10/2009 | Imai et al. |
| 7,624,006 B2 | 11/2009 | Chelba et al. |
| 7,672,940 B2 | 3/2010 | Viola et al. |
| 7,765,113 B2 | 7/2010 | Ware et al. |

(Continued)

OTHER PUBLICATIONS

International Search Report and Written Opinion for PCT/US2012/051096, dated Nov. 2, 2012.

(Continued)

*Primary Examiner* — Jonathan Ng
(74) *Attorney, Agent, or Firm* — Cooley LLP

(57) ABSTRACT

In some embodiments, a non-transitory processor-readable medium includes code to cause a processor to send a signal representing a first question and a set of pictogram answers associated with the first question and a second question, different from the first question, and a set of pictogram answers associated with the second question. The first question and the second question can define a health-related survey such as a health-risk assessment. The non-transitory processor-readable medium includes code to receive a user selection of a pictogram answer associated with the first question and receive a user selection of a pictogram answer associated with the second question. The non-transitory processor-readable medium includes code to define a health-related user profile based on the user selection to the first question and the second question.

12 Claims, 10 Drawing Sheets

(56) References Cited

U.S. PATENT DOCUMENTS

| | | | |
|---|---|---|---|
| 7,970,767 B2 | 6/2011 | Probst et al. | |
| 2001/0052122 A1 | 12/2001 | Nanos et al. | |
| 2002/0035486 A1* | 3/2002 | Huyn et al. | 705/3 |
| 2002/0062248 A1* | 5/2002 | Sakurai | 705/14 |
| 2003/0135095 A1* | 7/2003 | Iliff | 600/300 |
| 2003/0151630 A1* | 8/2003 | Kellman et al. | 345/838 |
| 2004/0138924 A1* | 7/2004 | Pristine | 705/2 |
| 2004/0181432 A1 | 9/2004 | Senba et al. | |
| 2005/0165627 A1 | 7/2005 | Fotsch et al. | |
| 2005/0273359 A1* | 12/2005 | Young | 705/2 |
| 2006/0253365 A1 | 11/2006 | Langshur et al. | |
| 2007/0021984 A1 | 1/2007 | Brown | |
| 2007/0028666 A1 | 2/2007 | Sasaki et al. | |
| 2007/0219776 A1 | 9/2007 | Gamon et al. | |
| 2007/0282666 A1* | 12/2007 | Afeyan et al. | 705/10 |
| 2010/0125564 A1 | 5/2010 | Strohm et al. | |
| 2010/0158616 A1 | 6/2010 | Kishida | |
| 2011/0046980 A1 | 2/2011 | Metzler et al. | |
| 2011/0046981 A1 | 2/2011 | Metzler et al. | |
| 2011/0047508 A1 | 2/2011 | Metzler et al. | |
| 2011/0099027 A1 | 4/2011 | Weathers | |
| 2012/0270201 A1 | 10/2012 | Cacioppo et al. | |
| 2012/0295676 A1 | 11/2012 | Ackerson et al. | |
| 2013/0212109 A1 | 8/2013 | Evancich et al. | |

OTHER PUBLICATIONS

U.S. Appl. No. 13/587,588, filed Aug. 16, 2012.
Office Action for U.S. Appl. No. 13/404,801, dated Feb. 24, 2012.
Popova, Maria. "Feeling Thoughts, Playing Visions | Brain Pickings". Retrieved Jan. 11, 2008 (http://www.brainpickings.org/index.php/2008/01/11/feeling-thoughts-playing-visions/).
Final Office Action for U.S. Appl. No. 13/404,801, dated Feb. 7, 2013.
Office Action for U.S. Appl. No. 13/587,588, dated Oct. 15, 2013.
Office Action for U.S. Appl. No. 13/404,801, dated May 21, 2014.
Office Action for U.S. Appl. No. 13/404,801, dated Jun. 17, 2015.

\* cited by examiner

1000

```
┌─────────────────────────────────────────────────────────────────────────┐
│ Send a signal representing a first question and a plurality of pictogram answers │
│                          for the first question                         │
│                                  1002                                   │
└─────────────────────────────────────────────────────────────────────────┘
                                      ↓
┌─────────────────────────────────────────────────────────────────────────┐
│ Receive a user selection of a pictogram answer from the plurality of pictogram │
│                     answers for the first question                      │
│                                  1004                                   │
└─────────────────────────────────────────────────────────────────────────┘
                                      ↓
┌─────────────────────────────────────────────────────────────────────────┐
│ Send a signal representing a second question and a plurality of pictogram │
│                     answers for the second question                     │
│                                  1006                                   │
└─────────────────────────────────────────────────────────────────────────┘
                                      ↓
┌─────────────────────────────────────────────────────────────────────────┐
│ Receive a user selection of a pictogram answer from the plurality of pictogram │
│                    answers for the second question                      │
│                                  1008                                   │
└─────────────────────────────────────────────────────────────────────────┘
                                      ↓
┌─────────────────────────────────────────────────────────────────────────┐
│ Define a health-related user profile based on the user selection for the first │
│         question and the user selection for the second question         │
│                                  1010                                   │
└─────────────────────────────────────────────────────────────────────────┘
```

FIG. 10

SYSTEMS AND METHODS FOR A HEALTH-RELATED SURVEY USING PICTOGRAM ANSWERS

CROSS-REFERENCE TO RELATED APPLICATION

This application claims priority to and the benefit of U.S. Provisional Patent Application Ser. No. 61/524,915, filed Aug. 18, 2011, entitled "System and Method for Exchanging Healthcare Information," the disclosure of which is hereby incorporated by reference in its entirety.

BACKGROUND

Embodiments described herein relate generally to a health-related survey such as a health risk assessment, and more particularly apparatus and methods for a health-related survey using pictogram answers.

With the development and popularity of online social networking sites, people can share and connect with other people having similar interests. Additionally, companies can collect useful information associated with the users of the social networking sites and use the information to direct ads, news articles, pictures, contact information, and/or the like to a given user. For example, a health care provider may desire information associated with a given customers lifestyle in connection with health care services.

Health care is an important aspect of today's society and with health care costs continually rising, much focus has been placed on prevention and healthy lifestyles. Often, developing a healthy lifestyle can be challenging and people may want to seek information, ideas, encouragement, and/or the like. To provide such things, surveys can be used to gather information about a person's lifestyle, as it pertains to health, to be able to deliver individualized information to the person. Unfortunately, some people may find known surveys boring and may lack the motivation to complete known surveys.

Thus, a need exists for systems and methods for a health-related survey using pictogram answers to define a health-related user profile.

SUMMARY

In some embodiments, a non-transitory processor-readable medium includes code to cause a processor to send a signal representing a first question and a set of pictogram answers associated with the first question and a second question, different from the first question, and a set of pictogram answers associated with the second question. The first question and the second question can define a health-related survey such as a health risk assessment. The non-transitory processor-readable medium includes code to receive a user selection of a pictogram answer associated with the first question and receive a user selection of a pictogram answer associated with the second question. The non-transitory processor-readable medium includes code to define a health-related user profile based on the user selection to the first question and the second question.

BRIEF DESCRIPTION OF THE DRAWINGS

FIG. 10 is a flowchart illustrating a method of using a social health system, according to an embodiment.

DETAILED DESCRIPTION

In some embodiments, a non-transitory processor-readable medium includes code to cause a processor to send a signal representing a first question and a set of pictogram answers associated with the first question and a second question, different from the first question, and a set of pictogram answers associated with the second question. The first question and the second question can define a health-related survey such as a health-risk assessment. The non-transitory processor-readable medium includes code to receive a user selection of a pictogram answer associated with the first question and receive a user selection of a pictogram answer associated with the second question. The non-transitory processor-readable medium includes code to define a health-related user profile based on the user selection to the first question and the second question.

In some embodiments, a non-transitory processor-readable medium includes code to cause a processor to send a signal representing a dashboard within a session at a first time. The dashboard includes a first question and a set of pictogram answers and is configured to receive a user-selected pictogram answer to the first question. The non-transitory processor-readable medium further including code to cause a processor to send a signal within the session at a second time representing the dashboard including a second question, different from the first, and a set of pictogram answers. The first question and the second question define a health-related survey such as a health-risk assessment. The code includes code to receive a user-selected pictogram answer to the second question through the dashboard and define a health-related user profile based on the user selection to the first question and the second question.

In some embodiments, a survey module can be configured to send a signal representing a first question and a set of pictogram answers associated with the first question and a second question, different from the first question, and a set of pictogram answers associated with the second question. The first question and the second question can define a health-related survey such as a health-risk assessment. A database can be operably coupled to the survey module and can be configured to store a health-related user profile associated with a user selection of a pictogram answer to the first question and the second question.

As used in this specification, the singular forms "a," "an" and "the" include plural referents unless the context clearly dictates otherwise. Thus, for example, the term "network" is intended to mean a single network or a combination of networks.

Figure 1:
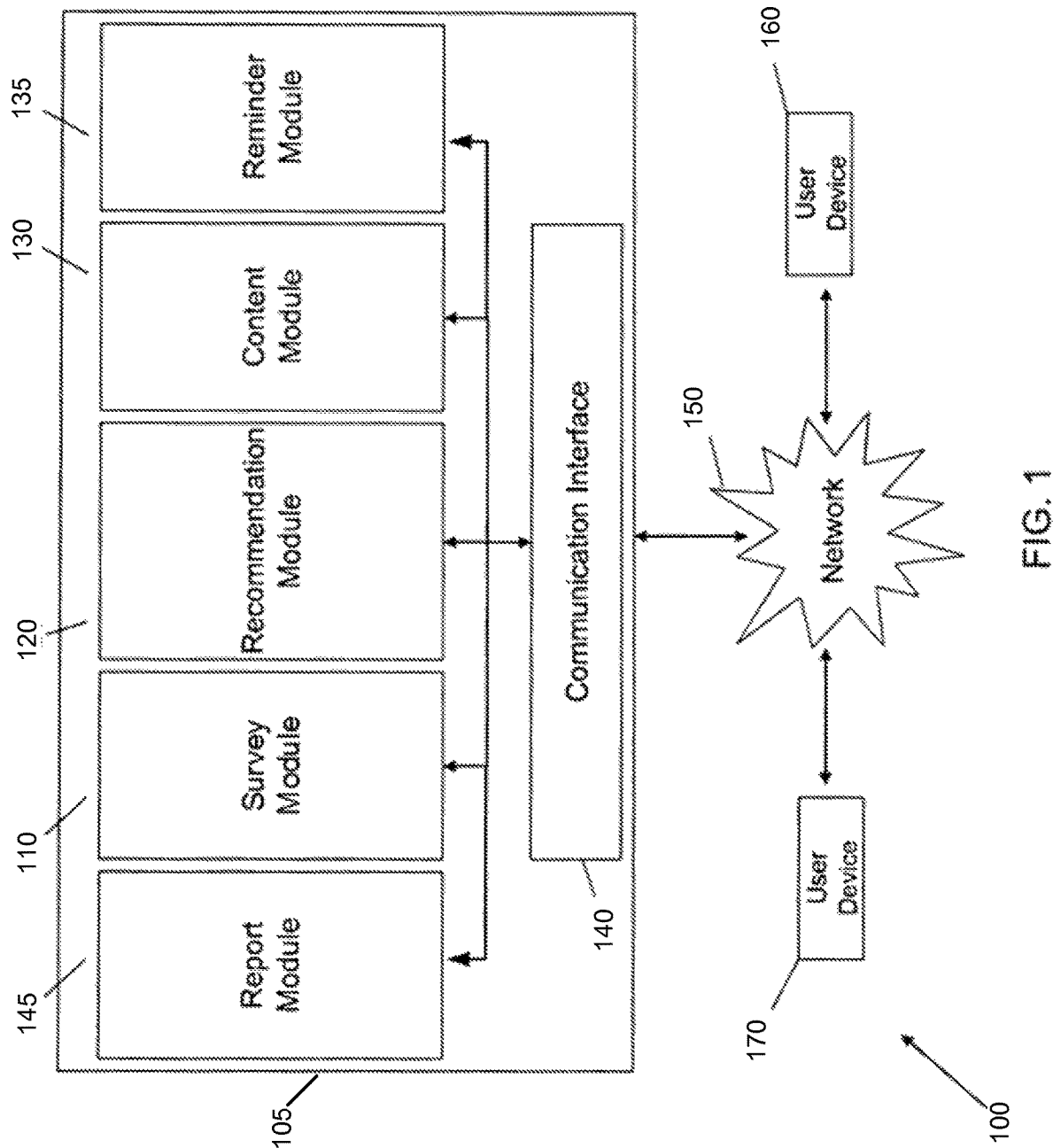
FIG. 1 is a schematic illustration of a social health system, according to an embodiment.

FIG. 1 is a schematic illustration of a social health system 100 that includes a host 105 in communication with one or more devices (e.g., an electronic device 160 and/or electronic device 170) via a network 150, according to an embodiment. The electronic device 160 can be, for example, a personal computer, a personal digital assistant (PDA), a smart phone, a video game console and/or the like. The electronic device 170 can be similar to the electronic device 160 or can be any other suitable electronic device described herein. The host 105 can be any suitable host device (e.g., a web server, a network of servers, a network management device, and/or the like). The network 150 can be any type of network (e.g., a local area network or LAN, a wide area network or WAN, a virtual network, a telecommunications network, and/or the internet) implemented as a wired network and/or a wireless network. As described in further detail herein, in some embodiments, for example, the electronic device 160 is a personal computer connected to the host 105 via an Internet Service Provider (ISP) and the Internet (e.g., network 150).

In some embodiments, the electronic device 160 can communicate with the host 105 and the network 150 via intermediate networks and/or alternate networks (not shown). Such intermediate networks and/or alternate networks can be of a same type or a different type of network as network 150. As such, in some embodiments, the electronic device 160 can send data to and/or receive data from the host 105 using multiple communication modes (e.g., via a website, email, instant messages, barcode transmissions, using a mobile device application, using a personal computer (PC) application, short message service (SMS), etc.) that may or may not be transmitted to the host 105 using a common network. For example, the electronic device 160 can be a mobile telephone (e.g., smart phone) connected to the host 105 via a cellular network and the Internet (e.g., network 150).

The host 105 can be any type of device or devices configured to send data over the network 150 to and/or receive data from one or more electronic device (e.g., the electronic device 160 and/or the electronic device 170). In some embodiments, the host 105 can be configured to function as, for example, a server device (e.g., a web server device), a network management device, and/or so forth. In some embodiments, the host 105 includes a processor and a memory configured to execute a given set of software modules. In other embodiments, the host 105 includes a processor (not shown in FIG. 1) and a memory (not shown in FIG. 1) configured to be operably coupled to a given set of hardware modules.

The memory (not shown) included in the host 105 can be, for example, a random access memory (RAM), a memory buffer, a hard drive, a read-only memory (ROM), an erasable programmable read-only memory (EPROM), and/or so forth. In some embodiments, the memory of the host 105 includes a set of instructions used to send a set of questions and answers to the electronic device 160 and/or the electronic device 170, receive a set of answers from the electronic device 160 and/or the electronic device 170, and define a health-related user profile based on the received answers. The health-related user profile can include, for example, user identifying information, health information about the user, and/or prescribed medications, as well as a user-controlled calendar, to-do lists, lists of friends, coaches, doctors, trainers, etc. Modules, as further described herein, can be configured to access the information contained in the user profile to display reminders for appointments, recommend online content, direct advertisements for medications, and/or the like.

The processor (not shown) can be any suitable processor such as, for example, a general purpose processor, a central processing unit (CPU), a network processor, a front end processor, and/or the like. As such, the processor is configured to perform a set of instructions stored in the memory. For example, the processor can be configured to send a signal representing a question with a plurality of pictogram answers to the electronic device 160 such that the question and answers are displayed on a screen of the electronic device 160 (e.g., via a web page viewed using an internet web browser).

The host 105 can be configured to execute specific modules and communicate with the network 150 via a communication interface 140. The modules can be, for example, hardware modules, software modules stored in the memory and executed by the processor, and/or any combination thereof. The modules can include a survey module 110, a recommendation module 120, a content module 130, a reminder module 135, and a report module 145.

The communication interface 140 is configured to communicate with the network 150 and more specifically the electronic device 160 or the electronic device 170. For example, the communication interface 140 can be a network card configured to communicate over a network such as, for example, a Local Area Network (LAN), a Wide Area Network (WAN), the internet, a cellular network via SMS or email, and/or any combination thereof. In some embodiments, the communication interface 140 can be configured to communicate over a specific network based on information within a user profile. For example, a user profile may include information indicating the user would like reminders sent over a cellular network via SMS, pop-ups, push notification, and/or the like. In some embodiments, the communication interface 140 can be configured to communicate with a social media platform such as, Facebook®, Twitter®, Google+®, and/or the like. For example, a user can define an indication within a health-related user profile allowing the communication interface 140 to access information stored in a Facebook® user profile.

As described in further detail herein, the survey module 110 is configured to generate and update a profile for one or more users based on questions provided to the users. The questions provided to the users can be referred to as a health-related survey such as a health risk assessment. For example, a set of questions with a set of pictogram answers can be sent to the electronic device 160 and based on the user-selected answers received from the electronic device 160, a user profile can be defined and/or updated for the user of the electronic device 160. More specifically, a user can use the electronic device 160 to establish a user profile on the social health system 100 and the survey module 110 can be configured to send a signal representing a question and a set of pictogram answers over the network 150 via the communication interface 140.

The survey module 110 can be configured to classify each question sent to a user, for example, via one or more meta-tags associated with the question (e.g., categories, keywords, hyperlinks, and/or the like). In this manner, the information included in the meta-tag can allow the social health system 100 to define and/or update a user profile and facilitate content selections, recommendations, and/or presentations of information to one or more users (e.g., the user of the electronic device 160 and/or the electronic device 170).

The recommendation module 120 is configured to generate and/or identify content that can be relevant to the interests of a user. For example, in some embodiments, recommendations can be generated based on a user profile. In some embodiments, recommendations can be generated based on meta-tags, such as, for example, keywords, categories, and/or usage information (e.g., information obtained by a web cookie associated with online activity). In this manner, the recommendation module 120 is configured to provide content recommendations to a user, such as, recommendations for websites, chat rooms, blogs, articles, videos, apps, profiles, locations, Twitter® accounts, Facebook® profiles, and/or the like. Additionally, the recommendation module 120 can include a feedback loop configured to improve the quality and/or accuracy of the recommendations. For example, the recommendation module 120 can determine if a recommendation to, for example, an article was viewed and/or the time spent on a recommended website. In such embodiments, the recommendation module 120 can be configured to rank or classify recommendations based on the recommendations made to a user that were followed by that user. In still other embodiments, the recommendation module 120 can be configured to rank and/or classify recommendations based on a user based ranking system, such as, for example, stars, where a greater number of stars indicates a higher relevancy to a given user.

In some embodiments, the recommendation module 120 can include a database (not shown in FIG. 1) configured to store information associated with recommendations. For example, the database can be configured to store user rating information, feedback, comments, and/or the like. The database can be any suitable database, such as a relational database, a non-relational database with one or more relational table structures, and/or the like.

The recommendation module 120 can be configured to communicate with the communication interface 140 such that the communication interface 140 can provide a recommendation to the user over the network 150. For example, the communication interface 140 can communicate with the network 150 over the internet and send a signal such that the recommendation appears on a display of the electronic device 160. In such embodiments, the recommendation can be a hyperlink for the user to follow by clicking on or touching the portion of the display representing the recommendation, as described in further detail herein.

The content module 130 is configured to manage content associated with the social health system 100. The content module 130 can access and/or receive content from any suitable network, such as the network 150. Similarly stated, the content module 130 can access and/or receive content from other networks independent of the network 150. In some embodiments, the content module 130 can include a database configured store the content. Content can include any type of media or information determined to be relevant to a user. For example, in some embodiments content can include informational material, advertising material, health information, activity information, and/or any other suitable content relevant to a user.

In some embodiments, the content module 130 is configured to perform natural language processing techniques on content, such as, for example, an article, a discussion, a question, a profile, and/or the like. For example, the content module 130 can be structured as a natural-language classifier that implements deterministic, non-deterministic, and/or machine-learning code or algorithms to classify content. In this manner, the content module 130 can classify the content using keywords, categories, ratings, rankings, etc. In some embodiments, the content module 130 can include a database configured to store the content. In other embodiments, the content module 130 can be operably coupled to a database (e.g., the database is independent of the content module 130).

In some embodiments, the content module 130 is configured to retrieve and/or incorporate advertising or promotional information based on a user profile. For example, the content module 130 can retrieve and store content relevant to a user based on meta-tags (e.g., keywords) in the user profile. The recommendation module 120 can further be configured to retrieve the stored content and recommend the content to the user. For example, the user profile can contain a given keyword. Based on the keyword, the content module 130 can retrieve content, such as a discussion group, and store the content in a database (e.g., a database operably coupled to the content module 130). The recommendation module 120 can communicate with the content module 130 to provide the content to the user in the form of a recommendation.

The reminder module 135 is configured to generate one or more reminders associated with health or profile information to one or more users (e.g., the users of the electronic device 160 and/or the electronic device 170). The reminders can be automatically generated based on user information. For example, the reminder module 135 can generate a reminder based on prescribed intervals associated with a medicine listed on a user's profile. In some embodiments, the reminder module 135 can generate reminders based on user, administrator, and/or caregiver input. For example, the reminder module 135 can generate a reminder associated with a scheduled doctor's appointment based on a user-generated indication within the user profile.

In some embodiments, the reminder module 135 can communicate with the electronic device 160 over the network 150, via the communication interface 140. The reminder module 135 can generate reminders such as, for example, SMS, emails, telephone calls, application notifications, push notifications, pop-up notifications, and/or the like. Additionally, the reminder module 135 can generate one-time reminders, recurring reminders, reminders based on activity or location, and/or the like. For example, the reminder module 135 can generate a daily SMS reminder based on a predefined time a user takes a medication.

In some embodiments, the reminder module 135 can generate a reminder based on activity or a period of inactivity with the social health system 100. For example, the reminder module 135 can generate a reminder if a predetermined time period of inactivity associated with the social health system 100 is reached. The reminder can be, for example, a reminder associated with a user's progress towards a specific goal, profile completion, and/or other metric stored by the social health system 100. In addition, the reminder module 135 can receive information from the user to update and/or send a reminder to a different user. For example, a first user (e.g., the user of the electronic device 160) and a second user (e.g., the user of the electronic device 170) can be associated on the social health system 100 and can share a common goal. The first user can accomplish the goal and information associated with the accomplished goal can generate an indication received by the reminder module 135 to send a reminder to the second user to continue to strive towards the goal.

The report module 145 is configured to generate one or more reports associated with one or more users based on user profile information and/or user inputs. Additionally, the report module 145 can communicate with the communication interface 140 to deliver a report over the network 150. For example, the report module 145 can generate a report associated with the health of a user and distribute the report over the network 150 to the user. In some embodiments, the report module 145 can generate and distribute a report to a partner organization with permission from the user to receive the report (e.g., healthcare provider, insurance company, pharmaceutical company, wellness professional, and/or the like).

While not shown in FIG. 1, in some embodiments, the electronic device 160 and the electronic device 170 can include one or more network interface devices (e.g., a network interface card) configured to connect the electronic device 160 and/or 170 to the network 150. In some embodiments, the electronic device 160 and the electronic device 170 can be referred to as client devices and can include a processor, a memory, and a display.

The memory of the electronic device 160 and 170 can be, for example, a random access memory (RAM), a memory buffer, a hard drive, a read-only memory (ROM), an erasable programmable read-only memory (EPROM), and/or so forth. In some embodiments, the memory of the electronic devices 160 and 170 stores instructions to cause the processor to execute modules, processes, and/or functions associated with using a personal computer application, mobile application, an internet web browser, and/or the like. Furthermore, the memory stores instructions to cause the processor to send signal information to the display. In some embodiments, the electronic device receives a web cookie from the host 105. In such embodiments, the memory is configured to store the cookie such that the host 105 can access data associated with the cookie.

The processor of the electronic device 160 and 170 can be any suitable processing device configured to run and/or execute a set of instructions or code. For example, the processor can be a general purpose processor, a central processing unit (CPU), an accelerated processing unit (APU), and/or the like. As described above, the processor can be configured to run and/or execute a set of instructions or code stored in the memory associated with using a personal computer application, mobile application, an internet web browser, and/or the like. Additionally, in some embodiments, the processor can run and/or execute a set of instructions associated with receiving a cookie the host 105.

The display can be any suitable display configured to provide a user interface to the electronic device 160 and 170. For example, the display can be a cathode ray tube (CRT) monitor, a liquid crystal display (LCD) monitor, a light emitting diode (LED) monitor, and/or the like. The display can be configured to provide the user interface for a personal computer application, mobile application, internet web browser, and/or the like. In such embodiments, the display can be configured to graphically represent the social health system 100 or any part thereof.

Figure 2:
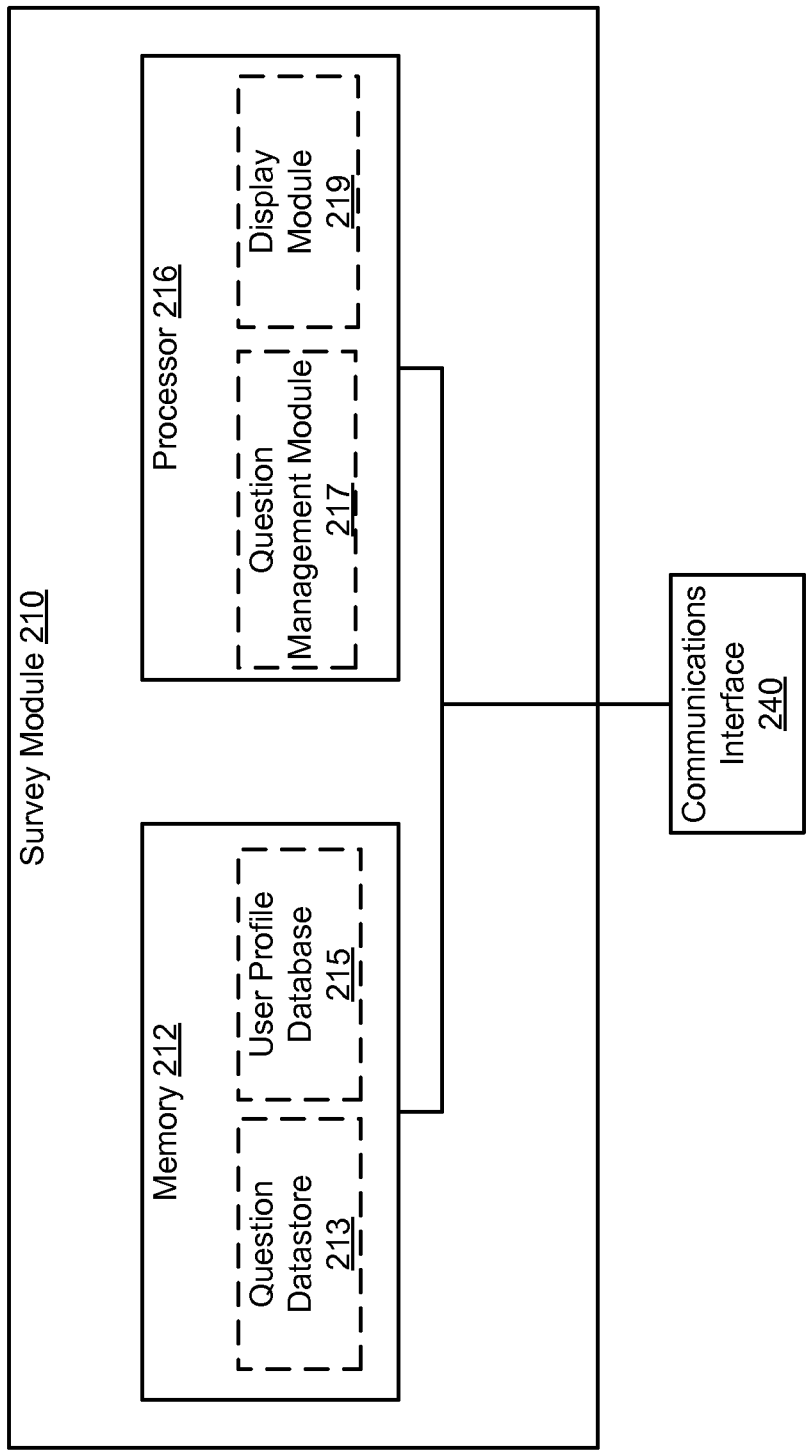
FIG. 2 is a schematic illustration of a survey module included in the social health system of FIG. 1.

FIG. 2 is a schematic illustration of a survey module 210 that includes a memory 212 and a processor 216 and is operably coupled to a communication interface 240 (e.g., a network card). Although FIG. 2 shows the memory 212 and the processor 216 being part of the survey module 210, it should be understood that the memory 212 and the processor 216 can also implement other modules such as the report module 145, the recommendation module 120, the content module 130, and/or the reminder module 135.

The survey module 210 is configured to send a signal representing a set of questions, each with a set of pictogram answers, and define a user profile based on the user selection of the pictogram answers. In some embodiments, the health-related user profile can include user identifying information, health information about the user, and/or prescribed medications, as well as a user-controlled calendar, to-do lists, lists of friends, coaches, doctors, trainers, etc. Modules, such as the recommendation module 120, the content module 130, the reminder module 135, and/or the report module 145, can be configured to access the information contained in the user profile to, display reminders for appointments, recommend online content, direct advertisements for medications, and/or the like. In some embodiments, questions can include standard questions triggered from or related to a user profile. In some embodiments, the questions can be received from healthcare providers, insurance companies, health or wellness organizations, and/or the like.

The survey module 210 can be configured to send health care questions to a user to develop and/or generate a health-related user profile. In some embodiments, a relatively small number (e.g., 10) questions can be sent to the user during an online session (e.g., a period of time spent on a health-care related webpage). In some embodiments, the user can be prompted to select whether the user would prefer to answer more questions during the session or defer to a second session to answer more questions. The user can also skip one or more questions and to answer other questions.

The survey module 210 can also be optionally configured to infer additional health-related information based on user-selected answers to the survey questions. For example, the survey module 210 can send questions to a user associated with the user's weight and activity level. If the user-selected answers contain information indicating, for example, the user is overweight and not active, the survey module 210 can further be configured to infer health-related information such as, for example, the user can be at risk for diabetes, heart disease, depression, and/or the like. The inferred health-related information can be associated with or included within the user profile, and can be stored in the user profile database 215 (discussed below). Additionally, the inferred health-related information can be accessed by, for example, an insurance company and/or healthcare provider. In some embodiments, the insurance company and/or healthcare provider can use the inferred information to validate their records.

The memory 212 can be, for example, a random access memory (RAM), a memory buffer, a hard drive, a read-only memory (ROM), an erasable programmable read-only memory (EPROM), and/or so forth. In some embodiments, the memory 212 of the survey module 210 stores instructions to cause the processor 216 to execute modules, processes, and/or functions associated with a social health system. Furthermore, the memory 212 stores instructions to cause the processor 216 to send a signal to the communication interface 240, such that information can be sent over a network (e.g., LAN, WAN, internet, cellular network, and/or the like.

The memory 212 includes and/or stores a question datastore 213 and a user profile database 215. The question datastore 213 can be a storage database configured to store question data. The question datastore 213 can be integrated with or operably coupled to (e.g., accessed via a network) the user profile database 215 and/or the processor 216. In some embodiments, the question datastore 213 can be one or more relational or non-relational databases that store question data, such as, for example, available questions, questions displayed to the users, answers to questions provided by users, one or more collections of questions with associated answers, logic or triggers associated with one or more of the questions and answers, and/or metadata associated with one or more of the questions and answers. In some embodiments, logic and/or metadata associated with one or more questions and answers can provide a relationship between two or more questions and answers stored in the question datastore 213. For example, a logical structure can indicate that questions should be presented to the user based on at least a part of a response to an earlier question. In some embodiments, the question datastore 213 includes multiple databases, including relational and non-relational database structures.

The user profile database 215 can be a storage database configured to store user profile information. The user database 215 can be integrated with or operably coupled to (e.g., accessed via a network) the question datastore 213 and/or the processor 216. In some embodiments, the user profile database 215 can be one or more relational or non-relational databases that store user profile information. In some embodiments, the user profile database 215 can be configured to store login information to verify a user's credentials when the user is accessing the user profile. For example, when a user enters login information into, for example, a website associated with a social health system, the processor 216 can be configured to retrieve the user profile information from the user profile database 215 and communicate with the communication interface 240 to deliver the user profile information to the user.

The health-related user profile within user profile database 215 can include, for example, user identifying information, health information about the user, and/or prescribed medications, as well as a user-controlled calendar, to-do lists, lists of friends, coaches, doctors, trainers, etc. Modules, as described herein, can be configured to access the information contained in the user profile to, display reminders for appointments, recommend online content, direct advertisements for medications, and/or the like. As described herein, health-related questions can be used to define the user profile. In addition, the survey module 210 can be optionally configured to infer a given set of health-related information based on the survey answers provided by the user and to store and/or associate the inferred health-related information within the user profile.

The processor 216 can be any suitable processor such as, for example, a general purpose processor, a central processing unit (CPU), a network processor, a front end processor, and/or the like. As such, the processor 216 is configured to perform a set of instructions stored in the memory 212. For example, the processor 216 can be configured to send a signal representing a question and a set of pictogram answers to the communication interface 240 for delivery to an electronic device such that the question and set of pictogram answers are displayed on a screen of the electronic device (e.g., via a web page viewed using an internet web browser.

The processor 216 includes a question management module 217 and a display module 219. The question management module 217 can be configured to manage and/or access information stored within the question datastore 213. For example, the question management module 217 can interact with and/or query the question datastore 213 using Structured Query Language (SQL), Contextual Query Language (CQL), and/or any other suitable programming language.

In some embodiments, the question management module 217 can be configured to present a thread of questions based on a users answers. For example, in some embodiments, the question management module 217 can present a first question and a set of pictogram answers and receive a user-selected pictogram answer. The question management module 217 can be configured to provide a first thread of questions if the answer to the first question is, for example, a "thumb up", and provide a second thread of questions in the answer to the first question is, for example, a "thumb down".

In some embodiments, the question management module 217 can receive user-selected answers and be configured to compare the answers to online information about the user. For example, in some embodiments, the question management module 217 can send a signal representing a question about alcohol consumption with a set of three pictogram answers, such as, for example, an empty glass (representing "I don't drink"), a half-full glass (representing "I drink a little"), and a full glass (representing "I drink regularly"). In such embodiments, if the user selects the empty glass pictogram answer (representing "I don't drink"), but the user's Facebook page indicates the user likes to go to bars, then the question management module 217 can be configured to tag the answer as being "suspect."

The display module 219 can be configured to generate a representation or layout containing one or more questions to a user. For example, questions can be presented to a user as part of a webpage encoded using a Hyper Type Markup Language (HTML) and/or the like. More specifically, the display module 219 can interact with the communication interface 240 such that the communication interface 240 sends a signal over the network representing the information from the display module 219. The display module 219 can generate HTML-encoded text, unformatted text, or one or more layouts based at least in part on user preference information, device information, accessibility information, and/or other information associated with a user or electronic device.

In some embodiments, a user interface, for example, a dashboard, can be generated by the display module 219. The dashboard, generated by the display module 219, can include an interface to elicit feedback and/or receive answers from one or more users. In some embodiments, the display module 219 can generate a dashboard that includes a health-related question and a set of pictogram answers. The dashboard can be configured such that the selection of a pictogram answer (e.g., clicking or touching the portion of the screen representing the answer) sends a signal representing the answer to the question management module 217. The dashboard can be configured in any suitable layout and/or configuration, such as, for example, those described below.

Figure 3:
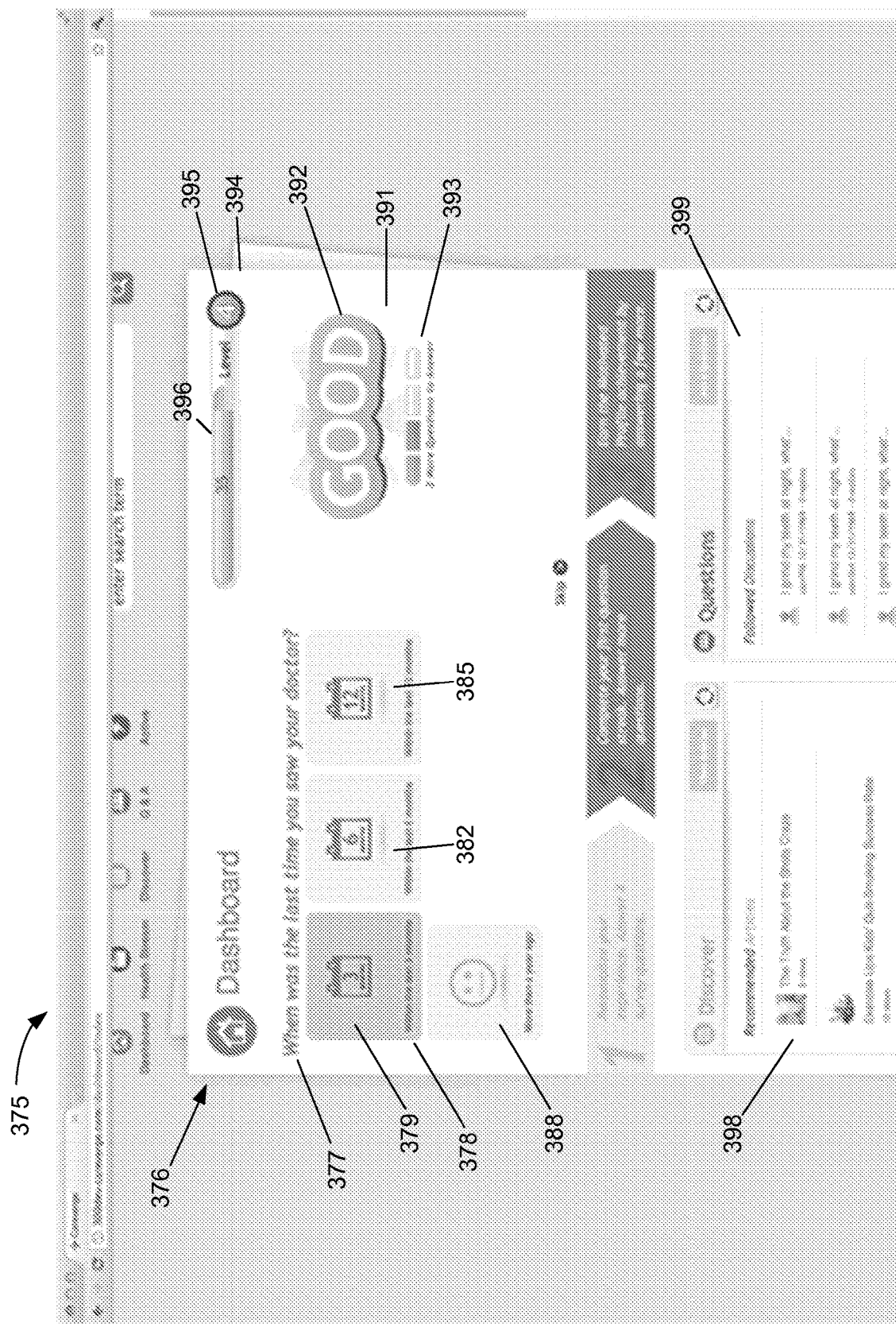
FIG. 3 is a screenshot of a social health system interface, according to an embodiment.

FIG. 3 is screenshot illustrating a social health system interface, according to an embodiment. The social health system interface can be established by any suitable hardware or software, such as those described herein, to cause a web browser 375 to display a dashboard 376. For example, a social health system interface can be established by a survey module (not shown in FIG. 3) similar to the survey module 210, described above with reference to FIG. 2. The web browser 375 can be any suitable web browser 375 included in an electronic device, such that the user of the web browser 375 can communicate through the social health system interface over a network (e.g., the internet).

The dashboard 376 can include a question portion 377, an answer portion 378, a badge portion 391, a level portion 394, a recommendation portion 398, and a discussion portion 399. In some embodiments, the dashboard 376 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 377.

In some embodiments, the dashboard 376 defines a given layout. Alternatively, in some embodiments, the dashboard can have a user-controlled layout. For example, in such embodiments, the dashboard 376 can be configured by the user such that the recommendation portion 398 is moved to the location of the discussion portion 399 and vice versa. In this manner, the layout shown on the screen of the user's electronic device can include the recommendation portion 398 and the discussion portion 399 in substantially opposite positions, as shown in FIG. 3.

The question portion 377 is configured to display a health-related question and can be a part of a health-related survey. The question portion 377 can be configured to display any suitable health-related question. For example, the question portion 377 can include questions about a user's health that could indicate to an insurance company or healthcare provider certain risk factors associated with the user's health. In some embodiments, the question portion 377 can be configured to display a question, at a first time, and a subsequent question, at a second time, after the first, while in a common online session. For example, as shown in FIG. 3, the question portion 377 includes a question that states, "When was the last time you saw your doctor?" The user-selected answer from the answer portion 378 can send a signal over a network to the social health system 100 (FIG. 1) such that the question display module 219 (FIG. 2) displays a subsequent question. Therefore, in such embodiments, the answering of a question displayed in the question portion 377 can be a trigger to display or cause the display of a subsequent question that is different from the first. In some embodiments, the answer to the question as selected by the user can trigger or cause a specific string of questions configured to gather more information about a given health-related topic.

The answer portion 378 included in the dashboard 376 is configured to display a set of pictogram answers to the question displayed in the question portion 377 and can be part of the health-related survey. The pictogram answers included in the answer portion 378 are configured to include a pictorial representation of a statement answering the question included in the question portion 377. For example, as shown in FIG. 3, the answer portion 378 includes a first pictogram answer 379, a second pictogram answer 382, a third pictogram answer 385, and a fourth pictogram answer 388, in response to the question, "When was the last time you saw your doctor?" In this embodiment, the first pictogram answer 379 includes a pictogram of a calendar including the number 3 and text that states, "Within the last 3 months." Therefore, the pictogram of the calendar including the number 3 is a pictorial representation of the statement, "Within the last 3 months." Similarly, the second pictogram answer 382 includes a pictogram of a calendar including the number 6 and text that states, "Within the last 6 months"; the third pictogram answer 385 includes a pictogram of a calendar including the number 12 and text that states, "Within the last 12 months"; and the fourth pictogram answer 390 includes a non-smiling face and text that states, "More than a year ago." In this manner, answer portion 378 including the pictorial representation of the answers can attempt to further engage a user when compared to answers in the foam of text alone. Furthermore, a user can find the set of pictogram answers more game-like and/or more fun to answer than text alone. Therefore, the user may be more likely to answer the set of pictogram answers compared to text only answers.

The pictogram answers displayed in the answer portion 378 can define any suitable number of answers in any suitable configuration, layout, shape, color, or size. In some embodiments, the pictogram answers can include a portion substantially similar. Alternatively, in some embodiments, each pictogram answer is substantially different for the other pictogram answers.

The answer portion 378 can be configured to send a signal to the social health system (e.g., the survey module 210 shown in FIG. 2) when a user selects a pictogram answer. For example, the display module 219 (FIG. 2) can display a question in the question portion 377 and display pictogram answers in the answer portion 378 as associated with computer code (e.g., HTTP and/or other programming language) configured to send a signal to the question management module 217 (FIG. 2) when the user selects a pictogram answer to the question. The question management module 217 can store the answer in any suitable manner, as described herein, to define or update a health-related user profile and can further be configured to send a signal to the display module 219 to send a signal representing a subsequent question. In this manner, when the user selects a pictogram answer to the question, the social health system can update the health-related user profile with the answer and update the dashboard to display the subsequent question.

The badge portion 391 is configured to provide encouragement to a user. For example, as shown in FIG. 3, the badge portion 391 displays a badge 392 that states, "GOOD." In some embodiments, the badge 392 displayed in the badge portion 391 is in response to the user-selected pictogram answer. In such embodiments, the user-selected pictogram answer can be associated with a score, where the healthiest answer results in the highest score. The score can further be associated with the badge 392 such that, the highest score (e.g., the healthiest answer) results in the badge 392 that states. "TERRIFIC!" In some embodiments, the badge portion 391 can be configured to display any suitable badge 392, such as those described above. In some embodiments, the badge portion 391 can be configured to display a graphic and or pictorial badge 392, such as, for example, a thumb up.

The badge portion 391 can also include an indicator 393 configured to show the user how many questions are left to answer in the user's current online session. For example, in some embodiments, the social health system can be configured to display four sequential questions in a common online session. Similarly stated, the social health system can be configured such that when a user selects a pictogram answer to a question, the dashboard 376 will display three more sequential questions, with each user-selected answer triggering or causing the next question to be displayed. Additionally, the indicator 393 will represent the number of questions answered during a common online session. In such embodiments, when the user selects a pictogram answer to a fourth question, the user has completed all the questions for the given online session and the indicator 393 can represent all the question were answered. In some embodiments, the indicator 393 can show the number of questions answered with shaded boxes, where the number of boxes shaded represents the number of questions answered and the number of unshaded boxes represents the number of questions left to answer. In this manner, the indicator 393 can be configured to represent the number of questions answered in a common online session.

As described above, the dashboard 376 includes a level portion 394. The level portion 394 is configured to display a level 395 a user has achieved towards the completion of the health-related user profile. For example, the level portion 394 shown in FIG. 3 shows the level 395 of a user as level "4." The level 395 is configured to increase as the user answers questions. In some embodiments, the level 395 can indicate to, for example, insurance providers, the involvement of a user. Additionally, the level 395 can provide a user encouragement to continue answering questions.

In some embodiments, the level portion 394 includes a status bar 396 configured to move along a range of positions between a first end position and a second end position. For example, the status bar 396 can indicate a user's position (e.g., level of completion) within a given level 395. In such embodiments, the status bar 396 can progress from left to right, with the end position on the left hand side being the beginning of a level and the end position of the right hand side being the end of a level (e.g., the completion of a level). The status bar 396 can be configured to move when a user selects a pictogram answer to a question displayed in the question portion 377. The level portion 394 can be configured in suitable way. For example, while shown in FIG. 3 as being a horizontal bar, the status bar 396 can be vertical and displayed below the level 395.

The recommendation portion 398 of the dashboard 376 can include recommendations from, for example, the recommendation module 120, shown in FIG. 1, or any other suitable portion of the social health system. The recommendation portion 398 can include any suitable recommendation such as, websites, chat rooms, blogs, articles, videos, apps, profiles, locations, Twitter® accounts, Facebook® profiles, and/or the like. In some embodiments, the recommendations displayed in the recommendation portion 398 can be hyperlinks, such that, by clicking on a recommendation the user is directed to, for example, a website reference in the recommendation. The recommendation portion 398 can be configured to display a graphical representation of a recommendation (e.g., a profile picture, a picture included in an article, a video, and/or the like) and/or a summary or portion of text included in the recommendation (e.g., a headline for an article).

In some embodiments, the recommendation portion 398 can display information associated with the number of users that viewed the recommendation and/or display user supplied information, such as comments, "likes" associated with Facebook®, "+1"s associated with Google+®, and/or the like. In this manner, the recommendation portion 398 can be configured to communicate with a portion of the social health system, for example, the recommendation module 120 (FIG. 1) to update the recommendation information. Additionally, the recommendation portion 398 can be configured to update the recommendations based on the user-selected answers to the questions displayed in the question portion 377. For example, as described above, the recommendation module 120 (FIG. 1) can include a feedback loop configured to receive information from the user profile such that the most relevant recommendations are displayed in the recommendation portion 398 at a given time.

The discussion portion 399 of the dashboard 376 can include a set of user asked health-related questions. In some embodiments, the discussion portion 399 can include hyperlinks to discussions in which a user is involved. For example, the discussion portion 399 can include a hyperlink to a discussion board within the social health system. In some embodiments, the discussion portion 399 included in the dashboard 376 can include discussions based on the user's question, while in some embodiments, the discussion portion 399 can include discussion followed by the user. In still other embodiments, the discussion portion 399 can include a combination of discussions based on the user's question and discussions followed by the user. In this manner, the discussion portion 399 can act as a shortcut to, for example, a discussion board.

Figure 4:
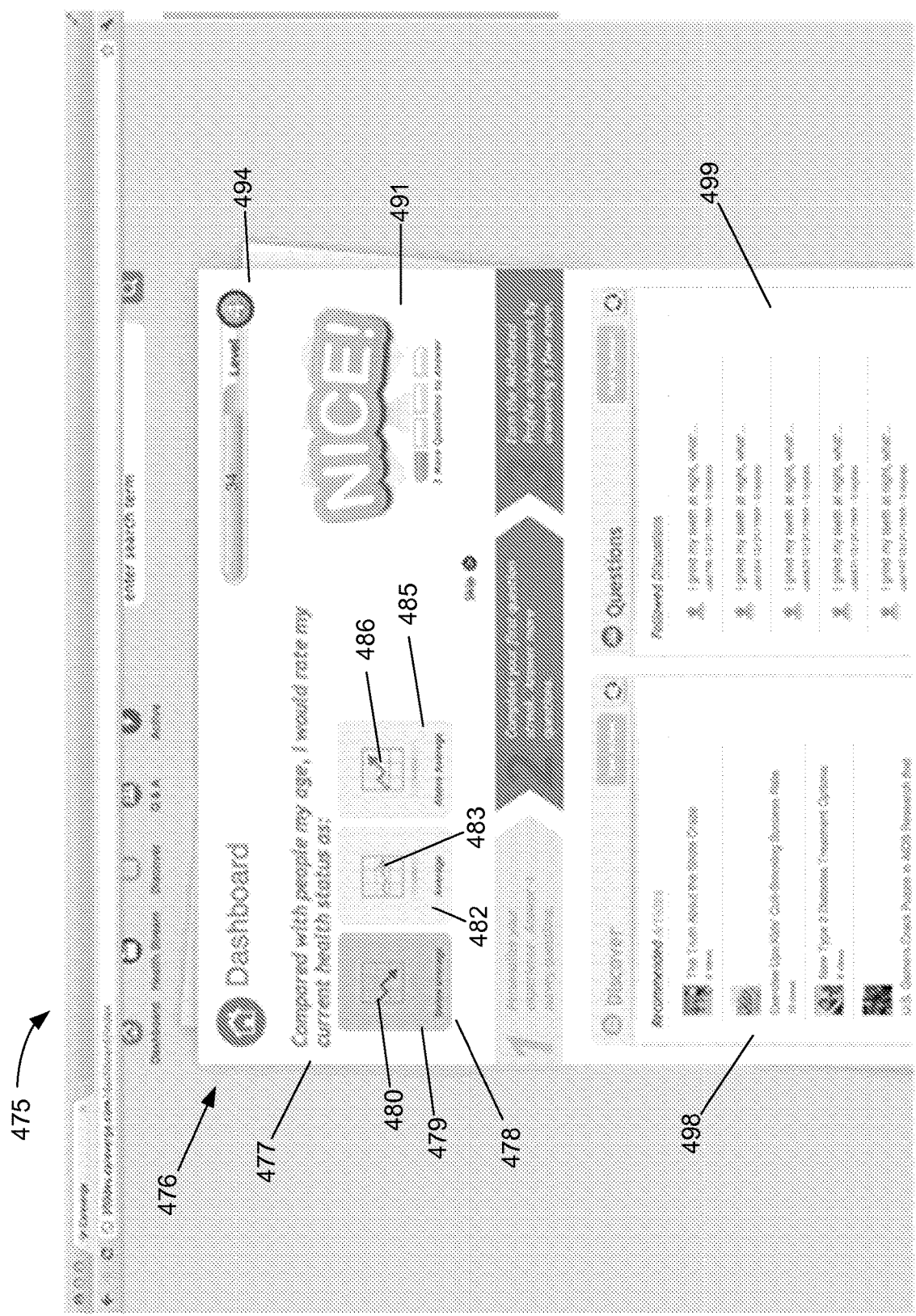
FIG. 4 is a screenshot of a social health system interface, according to an embodiment.

FIG. 4 is screenshot illustrating a social health system interface, according to an embodiment. The social health system interface can be established by any suitable hardware or software, such as those described herein, to cause a web browser 475 to display a dashboard 476. For example, a social health system interface can be established by a survey module (not shown in FIG. 4) similar to the survey module 210, described above with reference to FIG. 2. The web browser 475 can be any suitable web browser 475 included in an electronic device, such that the user of the web browser 475 can communicate through the social health system interface over a network (e.g., the internet).

The dashboard 476 can include a question portion 477, an answer portion 478, a badge portion 491, a level portion 494, a recommendation portion 498, and a discussion portion 499. In some embodiments, the dashboard 476 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 477.

In some embodiments, the dashboard 476 defines a given layout. Alternatively, in some embodiments, the dashboard can have a user-controlled layout. For example, in some embodiments, the dashboard 476 can be configured by the user such that the recommendation portion 498 is moved to the location of the discussion portion 499 and vice versa. In this manner, the layout shown on the screen of the user's electronic device can include the recommendation portion 498 and the discussion portion 499 in substantially opposite positions, as shown in FIG. 4.

The question portion 477, the answer portion 478, the badge portion 491, the level portion 494, the recommendation portion 498, and the discussion portion 499 of the dashboard 476 can be similar in function to the question portion 377, the answer portion 378, the badge portion 391, the level portion 394, the recommendation portion 398, and the discussion portion 399 of the dashboard 376. Therefore, some details of the portions included in the dashboard 476 are not described in detail herein and should be assumed to function similarly to the corresponding portion included in the dashboard 376, unless explicitly expressed otherwise. For example, the recommendation portion 498 included in the dashboard 476 functions similarly to the recommendation portion 398. In this manner, the recommendation portion 498 can be graphically represented similarly or can include updated recommendations when compared to the recommendation portion 398 while maintaining similar computer code, executed by a processor, which can govern the display of the recommendation portion 498.

The question portion 477 is configured to display a health-related question and can be a part of a health-related survey. For example, the question portion 477 can include questions about a user's health that could indicate to an insurance company or healthcare provider certain risk factors associated with the user's health. In some embodiments, the question portion 477 can be configured to display a question, at a first time, and a subsequent question, at a second time, after the first, while in a common online session. For example, as shown in FIG. 4, the question portion 477 includes a question that states, "Compared with people my age, I would rate my current health status as." The user-selected answer from the answer portion 478 can cause a signal to be sent over a network to the social health system (e.g., the social health system 105 shown in FIG. 1) such that the question display module 219 (FIG. 2) displays a subsequent question. Therefore, in such embodiments, the answering of a question displayed in the question portion 477 can trigger or cause display of a subsequent question that is different from the first. In some embodiments, the answer to the question as selected by the user can trigger or cause a specific string of questions configured to gather more information about a given health-related topic.

The answer portion 478 included in the dashboard 476 is configured to display a set of pictogram answers to the question displayed in the question portion 477 and can be part of the health-related survey. The pictogram answers included in the answer portion 478 are configured to include a pictorial representation of a statement answering the question included in the question portion 477. For example, as shown in FIG. 4, the answer portion 478 includes a first pictogram answer 479, a second pictogram answer 482, and a third pictogram answer 485, in response to the question, "Compared with people my age, I would rate my current health status as: ." In this embodiment, the first pictogram answer 479 includes a first pictogram 480 of a graph including a first directional indicator in a first, downward direction and includes text that states, "Below average." Therefore, the first pictogram 480 of the first directional indicator in the first, downward direction is a pictorial representation of the statement, "Below average." Similarly, the second pictogram answer 482 includes a second pictogram 483 of a graph including a second directional indicator in a second, horizontal direction and text that states, "Average", and the third pictogram answer 485 includes a third pictogram 486 of a graph including a third directional indicator in a third, upward direction and text that states, "Above average." In this manner, the directional indicators in the pictograms 480, 483, and 486 of the first pictogram answer 479, the second pictogram answer 483, and the third pictogram answer 484, respectively, can be assigned a value representing a level of health, with the first directional indicator associated with a lowest value, the second directional indicator associated with a middle value, and the third directional indicator associated with a highest value.

The answer portion 478 can be configured to send a signal to the social health system (e.g., the survey module 210 shown in FIG. 2) when a user selects a pictogram answer. For example, the display module 219 (FIG. 2) can display a question in the question portion 477 and display pictogram answers in the answer portion 478 associated with a computer code (e.g., HTTP and/or other programming language) configured to send a signal to the question management module 217 (FIG. 2) when the user selects a pictogram answer to the question. The question management module 217 can store the answer in, for example, the question datastore 213, or any suitable manner described herein, to define or update a health-related user profile and can further be configured to send a signal to the display module 219 to send a signal representing a subsequent question. In this manner, when the user selects a pictogram answer to the question, the social health system can define and/or update the health-related user profile with the answer and update the dashboard to display the subsequent question.

Figure 5:
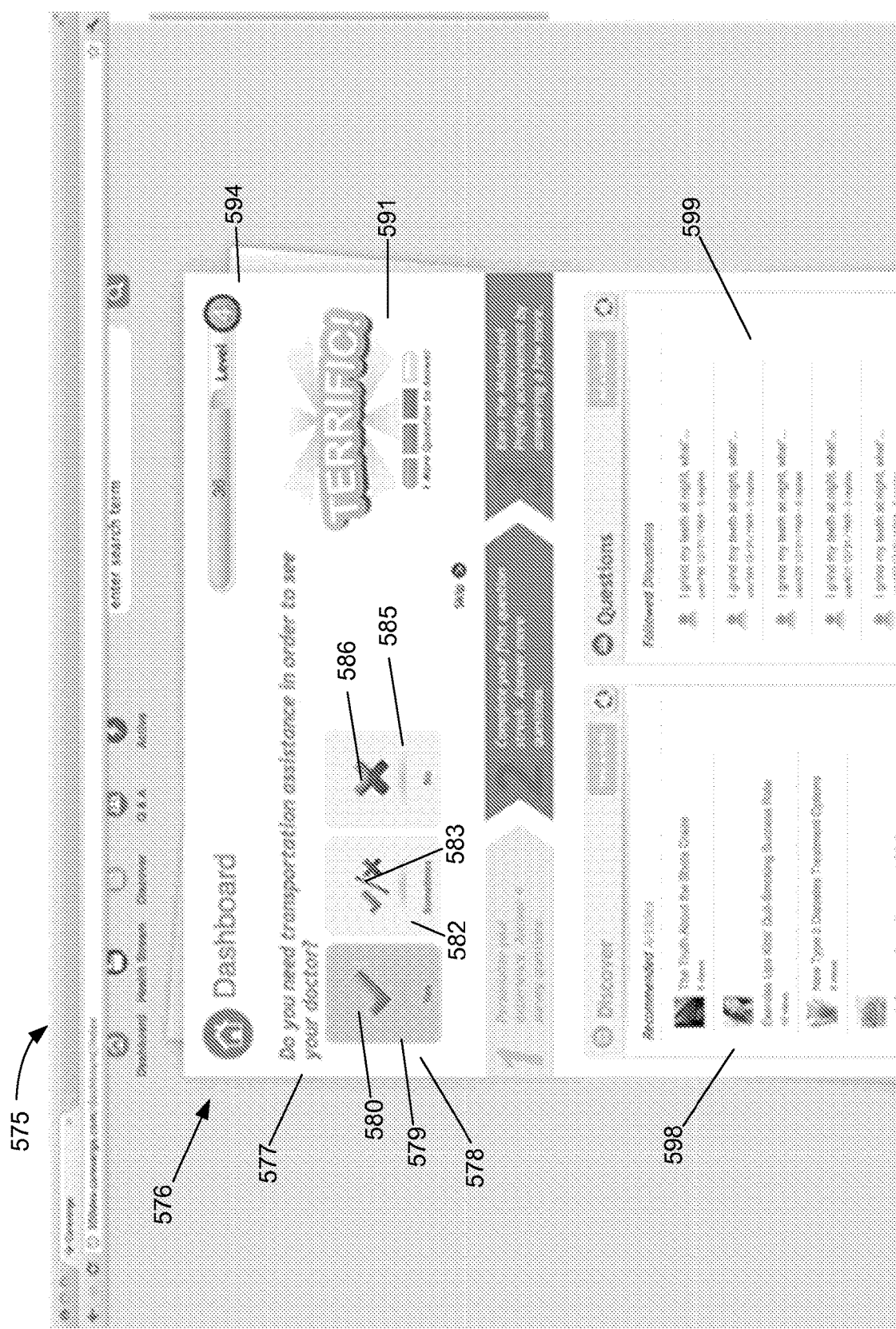
FIG. 5 is a screenshot of a social health system interface, according to an embodiment.

FIG. 5 is screenshot illustrating a social health system interface, according to an embodiment. The social health system interface can be established by any suitable hardware or software, such as those described herein, to cause a web browser 575 to display a dashboard 576. For example, a social health system interface can be established by a survey module (not shown in FIG. 5) similar to the survey module 210, described above with reference to FIG. 2. The web browser 575 can be any suitable web browser 575 included in an electronic device, such that the user of the web browser 575 can communicate through the social health system interface over a network (e.g., the internet).

The dashboard 576 can include a question portion 577, an answer portion 578, a badge portion 591, a level portion 594, a recommendation portion 598, and a discussion portion 599. In some embodiments, the dashboard 576 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 577.

In some embodiments, the dashboard 576 defines a given layout. Alternatively, in some embodiments, the dashboard 576 can include a user-controlled layout. For example, while shown in FIG. 5 as defining a specific layout, the dashboard 576 can be configured by the user such that the recommendation portion 598 is moved to the location of the discussion portion 599 and vice versa. In this manner, the layout shown on the screen of the user's electronic device can include the recommendation portion 598 and the discussion portion 599 in substantially opposite positions, as shown in FIG. 5.

The question portion 577, the answer portion 578, the badge portion 591, the level portion 594, the recommendation portion 598, and the discussion portion 599 of the dashboard 576 can be similar in function to the question portion 377, the answer portion 378, the badge portion 391, the level portion 394, the recommendation portion 398, and the discussion portion 399 of the dashboard 376. Therefore, some details of the portions included in the dashboard 576 are not described in detail herein and should be assumed to function similarly to the corresponding portion included in the dashboard 376, unless explicit expressed. For example, the recommendation portion 598 included in the dashboard 576 functions similarly to the recommendation portion 398. In this manner, the recommendation portion 598 can be graphically represented similarly or can include updated recommendations when compared to the recommendation portion 398 while maintaining similar computer code, executed by a processor, which can govern the display of the recommendation portion 598.

The question portion 577 is configured to display a health-related question and can be a part of a health-related survey. For example, the question portion 577 can include questions about a user's health that could indicate to an insurance company or healthcare provider certain risk factors associated with the user's health. In some embodiments, the question portion 577 can be configured to display a question, at a first time, and a subsequent question, at a second time, after the first, while in a common online session. For example, as shown in FIG. 5, the question portion 577 includes a question that states, "Do you need transportation assistance in order to see your doctor?" The user-selected answer from the answer portion 578 can send a signal over a network to the social health system (e.g., the social health system 105 shown in FIG. 1) such that the question display module 219 (FIG. 2) displays a subsequent question. Therefore, in such embodiments, the answering of a question displayed in the question portion 577 can trigger or cause display of a subsequent question that is different from the first. In some embodiments, the answer to the question as selected by the user can trigger or cause a specific string of questions configured to gather more information about a given health-related topic.

The answer portion 578 included in the dashboard 578 is configured to display a set of pictogram answers to the question displayed in the question portion 577 and can be part of the health-related survey. The pictogram answers included in the answer portion 578 are configured to include a pictorial representation of a statement answering the question included in the question portion 577. For example, as shown in FIG. 5, the answer portion 578 includes a first pictogram answer 579, a second pictogram answer 582, and a third pictogram answer 585, in response to the question, "Do you need transportation assistance in order to see your doctor?" In this embodiment, the first pictogram answer 579 includes a first pictogram 580 of a check mark and includes text that states, "Yes." Therefore, the first pictogram 580 of the check mark is a pictorial representation of the statement, "Yes." Similarly, the second pictogram answer 582 includes a second pictogram 583 of the check mark and an "X" and text that states, "Sometimes," and the third pictogram answer 585 includes a third pictogram 586 of the "X" and text that states, "No."

In this manner, the pictogram answers included in the answer portion 578 can include at least a portion that is similar to at least one other pictogram answer. More specifically, the first pictogram answer 579 includes the first pictogram 580 of the check mark, the second pictogram answer 582 includes the second pictogram 583 of the check mark and the "X", and the third pictogram answer 585 includes the third pictogram 586 of the "X". Therefore, a portion of the first pictogram answer 579 is configured to be similar to a portion of the second pictogram answer 582 and a portion of the third pictogram answer 585 is similar to a second portion of the second pictogram answer 582.

Figure 6:
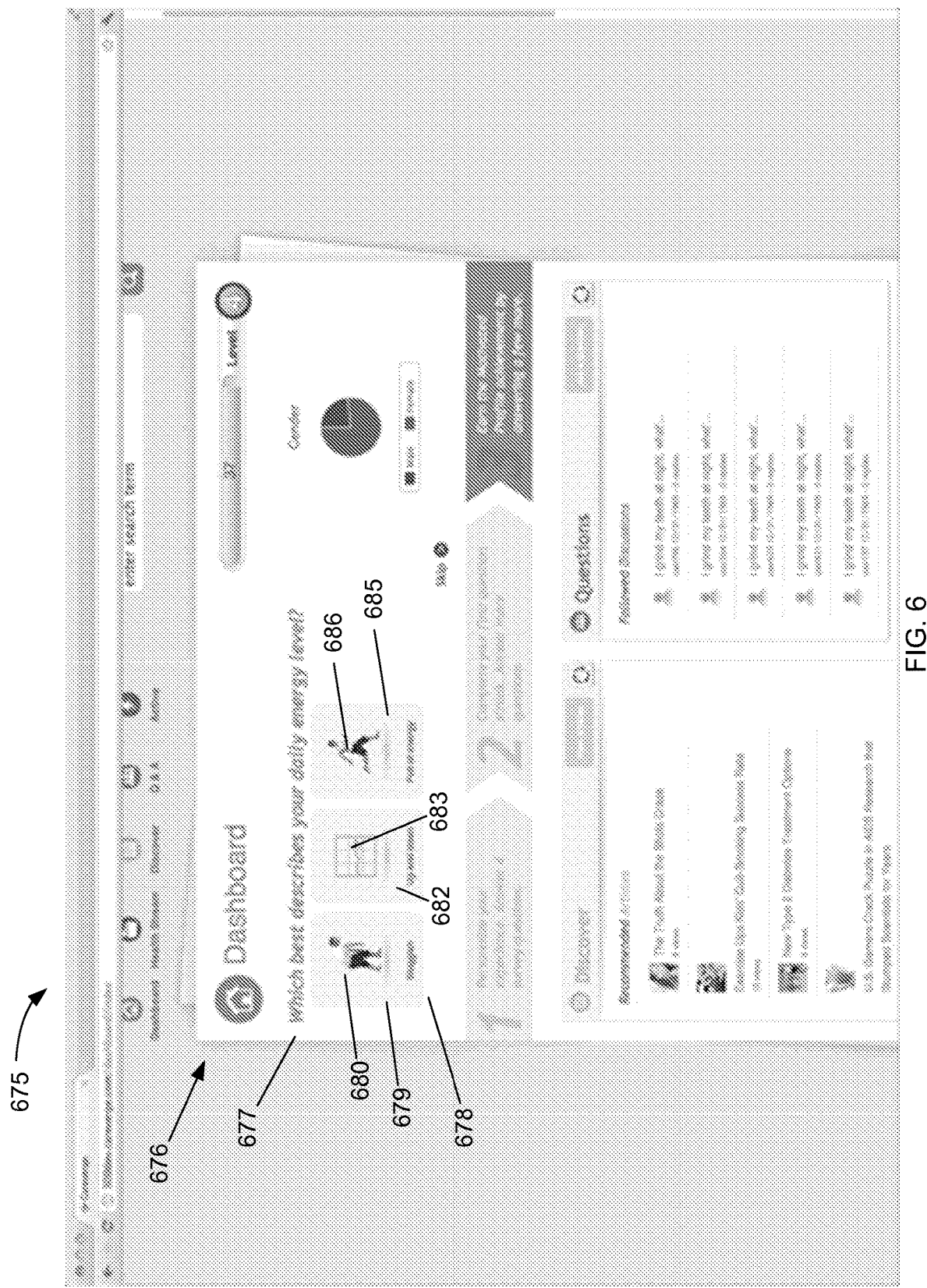
FIG. 6 is a screenshot of a social health system interface, according to an embodiment.

Alternatively, as shown in FIG. 6, a web browser 675 can be configured to show a dashboard 676 including a question portion 677, and an answer portion 678, such that a set of pictogram answers included in the answer portion 678 are dissimilar from each other. More specifically, the answer portion 678 can include a first pictogram answer 679, a second pictogram answer 682, and a third pictogram answer 685 in response to the question, "Which best describes your daily energy level?" displayed in the question portion 677 of the dashboard 376. The first pictogram answer 679 includes a first pictogram 680 of a person in a hunched position and text that states, "Sluggish." Therefore, the first pictogram 680 is a pictorial representation of the statement, "Sluggish." Similarly, the second pictogram answer 682 includes a second pictogram 683 of a graph with a directional indicator in a horizontal configuration and text that states, "Up and down", and the third pictogram answer 685 that includes a third pictogram 686 of a person running and text that states, "Full of energy." Therefore, as shown in FIG. 6, the first pictogram 680 of the first pictogram answer 679, the second pictogram 683 of the second pictogram answer 682, and the third pictogram 686 of the third pictogram answer 685 are substantially different from one another.

Figure 7:
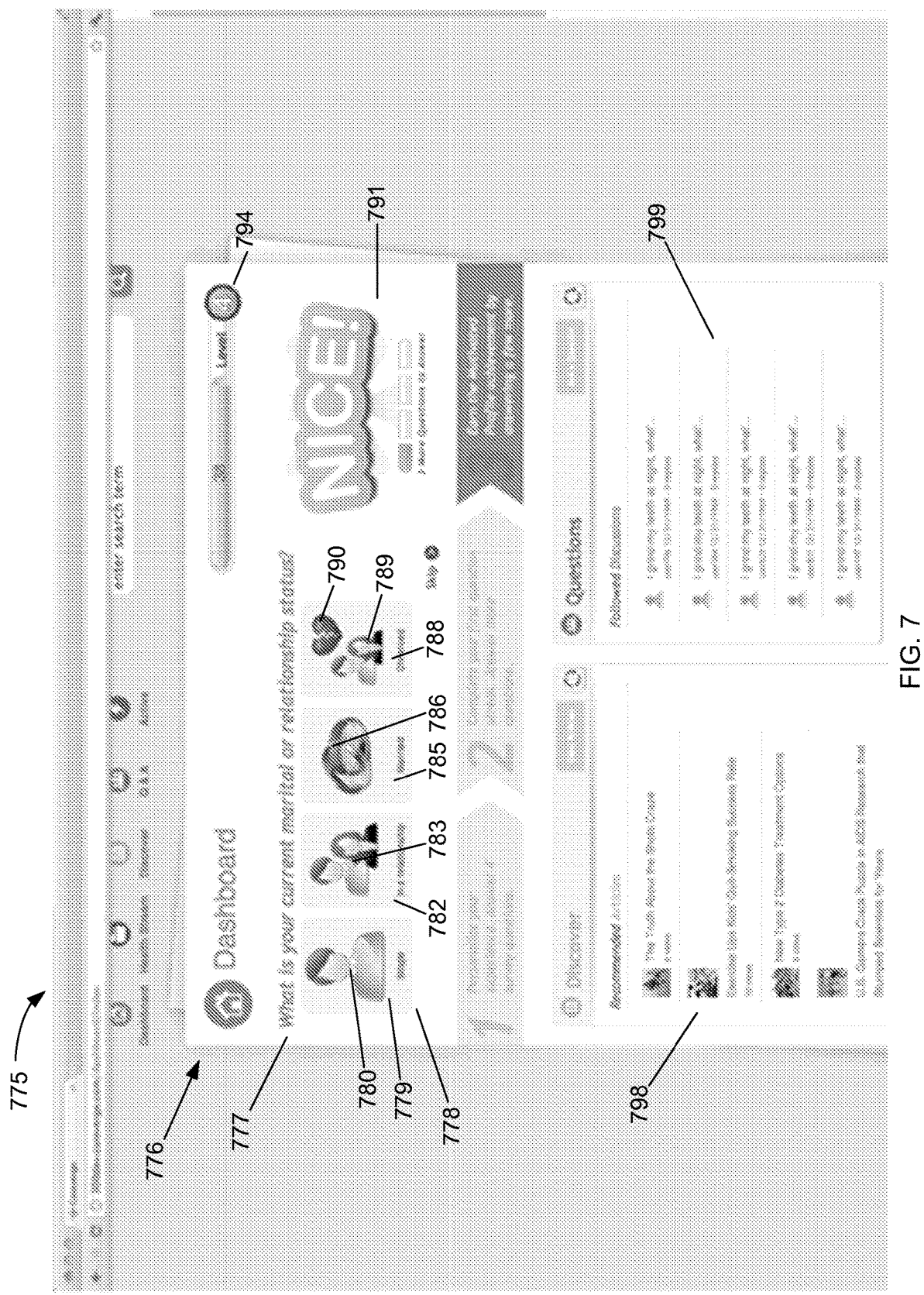
FIG. 7 is a screenshot of a social health system interface, according to an embodiment.

FIG. 7 is screenshot illustrating a social health system interface, according to an embodiment. The social health system interface can be established by any suitable hardware or software, such as those described herein, to cause a web browser 775 to display a dashboard 776. For example, a social health system interface can include a survey module (not shown in FIG. 7) similar to the survey module 210, described above with reference to FIG. 2. The web browser 775 can be any suitable web browser 775 included in an electronic device, such that the user of the web browser 775 can communicate through the social health system interface over a network (e.g., the internet).

The dashboard 776 can include a question portion 777, an answer portion 778, a badge portion 791, a level portion 794, a recommendation portion 798, and a discussion portion 799. In some embodiments, the dashboard 776 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 777.

The question portion 777, the answer portion 778, the badge portion 791, the level portion 794, the recommendation portion 798, and the discussion portion 799 of the dashboard 776 can be similar in function to the question portion 377, the answer portion 378, the badge portion 391, the level portion 394, the recommendation portion 398, and the discussion portion 399 of the dashboard 376. Therefore, some details of the portions included in the dashboard 776 are not described in detail herein and should be assumed to function similarly to the corresponding portion included in the dashboard 376, unless explicit expressed.

The question portion 777 is configured to display a health-related question and can be a part of a health-related survey. For example, the question portion 777 can include questions about a user's health that could indicate to an insurance company or healthcare provider certain risk factors associated with the user's health. In some embodiments, the question portion 777 can be configured to display a question, at a first time, and a subsequent question, at a second time, after the first, while in a common online session. For example, as shown in FIG. 7, the question portion 777 includes a question that states, "What is your current marital or relationship status?" The user-selected answer from the answer portion 778 can send a signal over a network to the social health system (e.g., the social health system 105 shown in FIG. 1) such that the question display module 219 (FIG. 2) displays a subsequent question. Therefore, in such embodiments, the answering of a question displayed in the question portion 777 can trigger or cause display of a subsequent question that is different from the first. In some embodiments, the answer to the question as selected by the user can trigger or cause a specific string of questions configured to gather more information about a given health-related topic.

The answer portion 778 included in the dashboard 778 is configured to display a set of pictogram answers to the question displayed in the question portion 777 and can be part of the health-related survey. The pictogram answers included in the answer portion 778 are configured to include a pictorial representation of a statement answering the question included in the question portion 777. For example, as shown in FIG. 7, the answer portion 778 includes a first pictogram answer 779, a second pictogram answer 782, a third pictogram answer 785, and a fourth pictogram answer 788 in response to the question, "What is your current marital or relationship status?" In this embodiment, the first pictogram answer 779 includes a first pictogram 780 of a man and includes text that states, "Single." Therefore, the first pictogram 780 is a pictorial representation of the statement, "Single." Furthermore, the answer portion 778 can be configured to note if the user is male or female based on the user profile information. In this manner, the answer portion 778 can be configured to display the first pictogram 780 of the man if the user profile indicates the user is a male and to display the first pictogram 780 of a woman if the user profile indicates the user is a female. The second pictogram answer 782 includes a second pictogram 783 of a male and female and text that states, "In a relationship." The second pictogram 783 of the second pictogram answer can be configured to include a portion that is similar to a portion of the first pictogram 780 of the first pictogram answer 779. For example, the first pictogram 780 includes the man and the second pictogram 783 includes the man and the woman. The third pictogram answer 785 includes a third pictogram 786 of wedding bands and text that states, "Married." The fourth pictogram answer 788 includes a fourth pictogram 789 of the man and woman and a fifth pictogram 790 of a broken heart and text that states, "Divorced." In this manner, the fourth pictogram answer 788 includes multiple pictograms to represent the text included in the fourth pictogram answer 788. In some embodiments, the fifth pictogram 790 can be in contact with the fourth pictogram 789. In other embodiments, the first, second, and/or third pictogram answer can include a plurality of pictograms.

Figure 8:
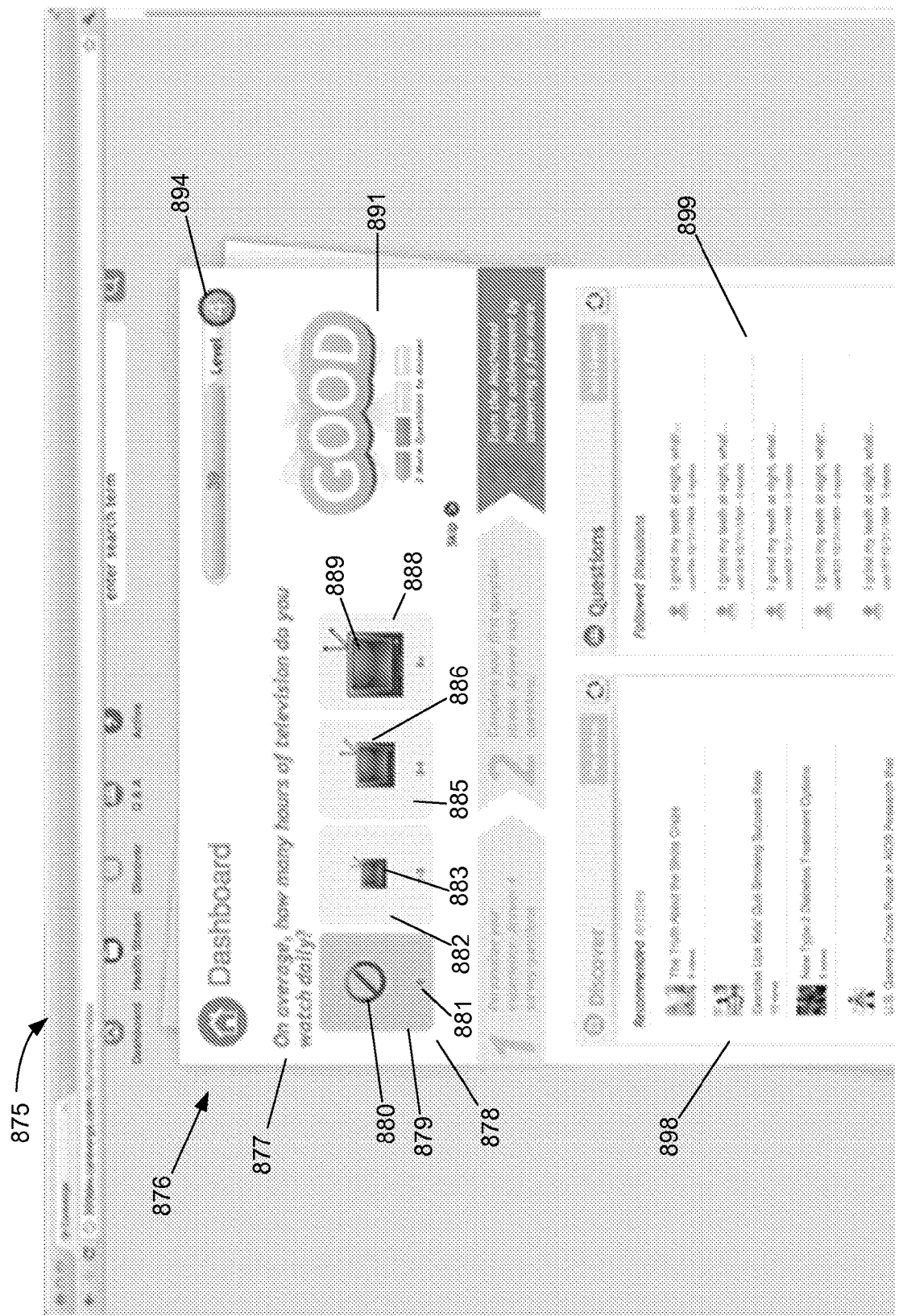
FIG. 8 is a screenshot of a social health system interface, according to an embodiment.

FIG. 8 is screenshot illustrating a social health system interface, according to an embodiment. The social health system interface can be established by any suitable hardware or software, such as those described herein, to cause a web browser 875 to display a dashboard 876. For example, a social health system interface can be established by a survey module (not shown in FIG. 8) similar to the survey module 210, described above with reference to FIG. 2. The web browser 875 can be any suitable web browser 875 included in an electronic device, such that the user of the web browser 875 can communicate through the social health system interface over a network (e.g., the internet).

The dashboard 876 can include a question portion 877, an answer portion 878, a badge portion 891, a level portion 894, a recommendation portion 898, and a discussion portion 899. In some embodiments, the dashboard 876 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 877.

The question portion 877, the answer portion 878, the badge portion 891, the level portion 894, the recommendation portion 898, and the discussion portion 899 of the dashboard 876 can be similar in function to the question portion 377, the answer portion 378, the badge portion 391, the level portion 394, the recommendation portion 398, and the discussion portion 399 of the dashboard 376. Therefore, some details of the portions included in the dashboard 876 are not described in detail herein and should be assumed to function similarly to the corresponding portion included in the dashboard 376, unless explicit expressed.

The question portion 877 is configured to display a health-related question and can be a part of a health-related survey. For example, the question portion 877 can include questions about a user's health that could indicate to an insurance company or healthcare provider certain risk factors associated with the user's health. In some embodiments, the question portion 877 can be configured to display a question, at a first time, and a subsequent question, at a second time, after the first, while in a common online session. For example, as shown in FIG. 8, the question portion 877 includes a question that states, "On average, how many hours of television of you watch daily?" The user-selected answer from the answer portion 878 can send a signal over a network to the social health system (e.g., the social health system 105 shown in FIG. 1) such that the question display module 219 (FIG. 2) displays a subsequent question. Therefore, in such embodiments, the answering of a question displayed in the question portion 877 can trigger or cause display of a subsequent question that is different from the first. In some embodiments, the answer to the question as selected by the user can trigger or cause a specific string of questions configured to gather more information about a given health-related topic.

The answer portion 878 included in the dashboard 878 is configured to display a set of pictogram answers to the question displayed in the question portion 877 and can be part of the health-related survey. The pictogram answers included in the answer portion 878 are configured to include a pictorial representation of a statement answering the question included in the question portion 877. For example, as shown in FIG. 8, the answer portion 878 includes a first pictogram answer 879, a second pictogram answer 882, a third pictogram answer 885, and a fourth pictogram answer 888 in response to the question, "On average, how many hours of television do you watch daily?" In this embodiment, the first pictogram answer 879 includes a first pictogram 880 of a no symbol and includes a value "0." Therefore, the first pictogram 880 of the no symbol is a pictorial representation of the value "0." The second pictogram answer 882 includes a second pictogram 883 of a television with a first size and a value "1-2." The third pictogram answer 885 includes a third pictogram 886 of the television with a second size, larger than the first, and a value "3-4." The fourth pictogram answer 888 includes a fourth pictogram 889 of the television with a third size, larger than the second size, and a value "5+." In this manner, the size of the second pictogram 883, the third pictogram 886, and the fourth pictogram 889 correspond to the second value, "1-2," the third value "3-4" (which is larger than the second), and the fourth value, "5+" (which is larger than the third). Therefore, the pictogram answers can be configured such that the size of the pictogram included in the pictogram answer is related to a value, such that the larger size equates to the larger value.

Figure 9:
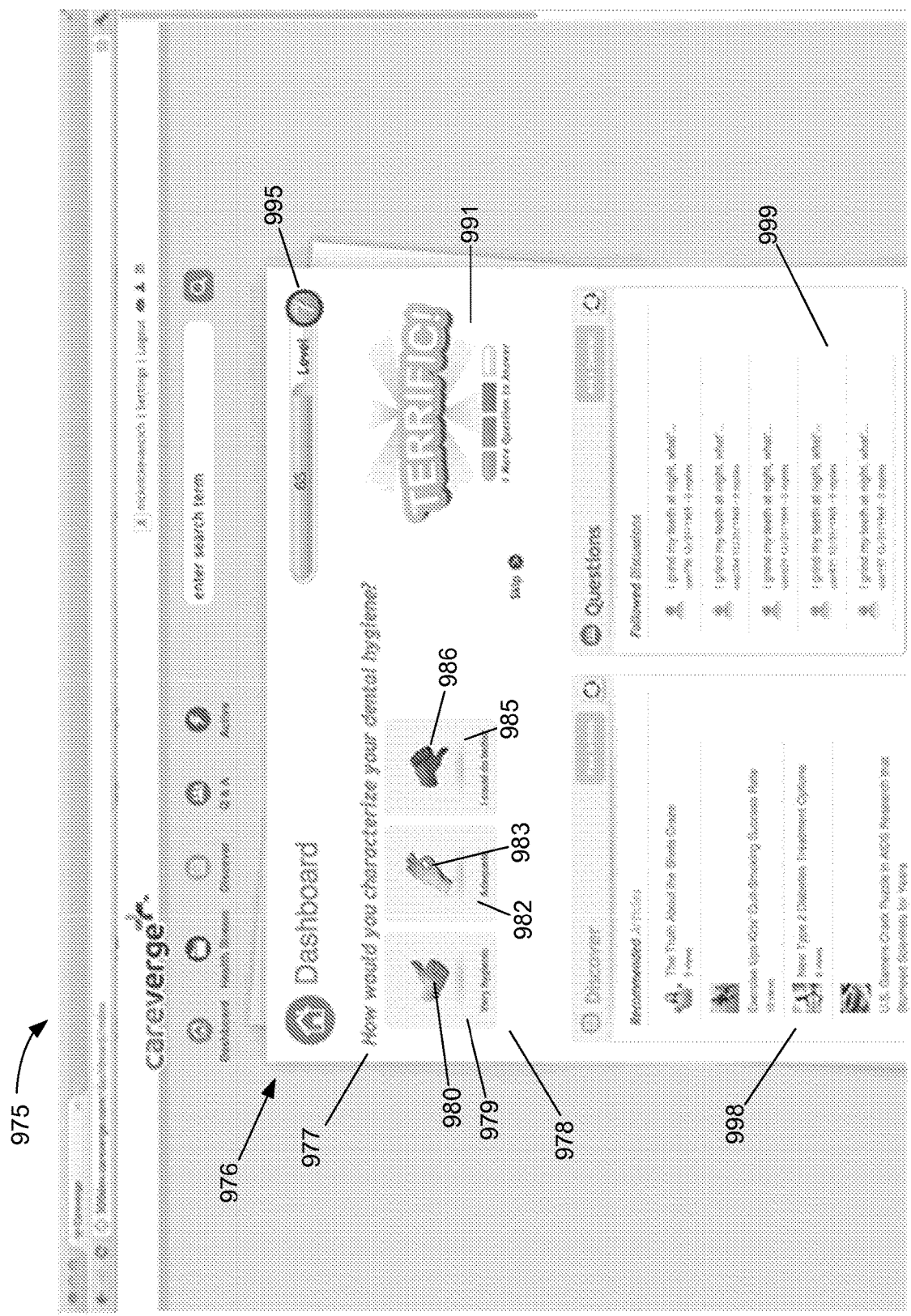
FIG. 9 is a screenshot of a social health system interface, according to an embodiment.

FIG. 9 is screenshot illustrating a social health system interface, according to an embodiment. The social health system interface can be established by any suitable hardware or software, such as those described herein, to cause a web browser 975 to display a dashboard 976. For example, a social health system interface can include a survey module (not shown in FIG. 9) similar to the survey module 210, described above with reference to FIG. 2. The web browser 975 can be any suitable web browser 975 included in an electronic device, such that the user of the web browser 975 can communicate through the social health system interface over a network (e.g., the internet).

The dashboard 976 can include a question portion 977, an answer portion 978, a badge portion 991, a level portion 994, a recommendation portion 998, and a discussion portion 999. In some embodiments, the dashboard 976 can define a health-related user profile configured to provide information to, for example, insurance companies, healthcare providers, caregivers, and/or the like. The health-related user profile can include user identifying information, health information about the user, and/or prescribed medications based on one or more questions contained in the question portion 977.

The question portion 977, the answer portion 978, the badge portion 991, the level portion 994, the recommendation portion 998, and the discussion portion 999 of the dashboard 976 can be similar in function to the question portion 377, the answer portion 378, the badge portion 391, the level portion 394, the recommendation portion 398, and the discussion portion 399 of the dashboard 376. Therefore, some details of the portions included in the dashboard 976 are not described in detail herein and should be assumed to function similarly to the corresponding portion included in the dashboard 376, unless explicit expressed.

The question portion 977 is configured to display a health-related question and can be a part of a health-related survey. For example, the question portion 977 can include questions about a user's health that could indicate to an insurance company or healthcare provider certain risk factors associated with the user's health. In some embodiments, the question portion 977 can be configured to display a question, at a first time, and a second question, at a second time, after the first, while in a common online session. For example, as shown in FIG. 9, the question portion 977 includes a question that states, "How would you characterize you dental hygiene?" The user-selected answer from the answer portion 978 can send a signal over a network to the social health system (e.g., the social health system 105 shown in FIG. 1) such that the question display module 219 (FIG. 2) displays a second question. Therefore, in such embodiments, the answering of a question displayed in the question portion 977 can trigger or cause display of a second question that is different from the first. In some embodiments, the answer to the question as selected by the user can trigger or cause a specific string of questions configured to gather more information about a given health-related topic.

The answer portion 978 included in the dashboard 978 is configured to display a set of pictogram answers to the question displayed in the question portion 977 and can be part of the health-related survey. The pictogram answers included in the answer portion 978 are configured to include a pictorial representation of a statement answering the question included in the question portion 977. For example, as shown in FIG. 9, the answer portion 978 includes a first pictogram answer 979, a second pictogram answer 982, and a third pictogram answer 985, in response to the question, "How would you characterize you dental hygiene?" In this embodiment, the first pictogram answer 979 includes a first pictogram 980 of a thumb up symbol and includes text that states "Very hygienic." Therefore, the first pictogram 980 of the thumb up symbol is a pictorial representation of the text "Very Hygienic." Similarly, the second pictogram answer 982 includes a second pictogram 983 of a hand sign for O.K. and text that states "Adequate," and the third pictogram answer 985 includes a third pictogram 986 of a thumb down symbol and text that states "I could do better."

In some embodiments, the discussion portion 999 can be filtered to display discussions that are associated with the question that is displayed in the question portion 977. More specifically, the topic of the question displayed in the question portion 977 can trigger or cause the discussion portion 999 to filter discussions displayed in the discussion portion 999 to said topic. For example, as shown in FIG. 9, the question associated with dental hygiene can trigger or cause the discussion portion 999 to filter out all discussions that are not associated with the topic of the question.

FIG. 10 is a flowchart illustrating a method 1000 for a health-related survey used to define a health-related profile as described herein. The method 1000 can be implemented by a social health system the can include a host in communication with at least one electronic device. The method 1000 can be used for example, to administer a health-related survey including a set of pictogram answers such as to develop a health-related user profile.

In some embodiments, the method 1000 includes sending a signal representing a first question and a set of pictogram answers for the first question, at 1002. For example, in some embodiments, the electronic device 160 is in communication with a host 105 via the network 150, described with respect to FIG. 1. The host can receive a user selection of a pictogram answer from the set of pictogram answers for the first question, at 1004. With the host having received the user selection of the pictogram answer to the first question, the host can send a signal representing a second question and a set of pictogram answers for the second question, at 1006. More specifically, the host can send the second signal representing the second question and the set of pictogram answers for the second question at a second time within a common session, after the host receives the user-selected pictogram answer to the first question. In some embodiments, the host device can send the signal representing the second question and the set of pictogram answers for the second question contemporaneously with the signal representing the first question and the set of pictogram answers for the first question. The host can receive a user selection of a pictogram answer from the set of pictogram answers for the second question, at 1008. The host can define a health-related user profile based on the user selection for the first question and the user selection for the second question, at 1010. For example, the dashboard 376 can represent a user profile for a given user, as described, with respect to FIG. 3.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals (e.g., a propagating electromagnetic wave carrying information on a transmission medium such as space or a cable). The media and computer code (also referred to herein as code) may be those designed and constructed for the specific purpose or purposes. Examples of non-transitory computer-readable media include, but are not limited to: magnetic storage media such as hard disks, optical storage media such as Compact Disc/Digital Video Discs (CD/DVDs), Compact Disc-Read Only Memories (CD-ROMs), magneto-optical storage media such as optical disks, carrier wave signal processing modules, and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using Java, C++, or other programming languages and/or other development tools.

While various embodiments have been described above, it should be understood that they have been presented by way of example only, and not limitation, and as such, various changes in form and/or detail may be made. Any portion of the apparatus and/or methods described herein may be combined in any suitable combination, unless explicitly expressed otherwise. Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed is:

1. A method, comprising:
presenting, via a graphical user interface (GUI), a first question and a plurality of pictogram answers for the first question including a first pictogram answer associated with a first numerical value, the first pictogram answer having a first size associated with a first numerical value and a second pictogram answer having a second size larger than the first size, the second size associated with a second numerical value larger than the first numerical value, the first question and the plurality of pictogram answers for the first question being presented via the GUI such that a user of the user device can select a first pictogram answer independent from any other individual;
receiving, via the GUI, a user selection of the first pictogram answer from the plurality of pictogram answers for the first question;
defining a health-related user profile based on the user selection for the first question;
determining, by a processor operably coupled to the GUI, that a second question is relevant to the health-related user profile of the user based on the selection of the first pictogram answer by the user, and that a third question is not relevant to the health related user profile based on the selection of the first pictogram answer, the third question being (1) different from the second question and (2) designated for selection when the user selects the second pictogram answer;
automatically presenting, via the GUI, the second question and a plurality of pictogram answers for the second question based on the determination that the second question is relevant to the health-related user profile, the second question being different from the first question, the plurality of pictogram answers for the second question being different from the plurality of pictogram answers for the first questions, the first question and the second question collectively defining at least portion of a health-related survey, the plurality of pictogram answers for the first question and the plurality of pictogram answers for the second answer configured to engage the user more than text-only answers;
receiving, via the GUI, a user selection of a pictogram answer from the plurality of pictogram answers for the second question; and
automatically updating the health-related user profile based on the user selection for the first question and the user selection for the second question.

2. The method of claim 1, wherein the the first question is presented, the user selection of the first pictogram answer for the first question is received, the second question is presented, and the pictogram answer for the second question is received, within a common session.

3. The method of claim 1, wherein the first pictogram answer has a directional indicator and the second pictogram answer has a directional indicator different from the directional indicator of the first pictogram answer, the directional indicator of the first pictogram answer being associated with a value, the directional indicator of the second pictogram answer being associated with a value different from the value associated with the first pictogram answer.

4. The method of claim 1, wherein the first pictogram answer has a first portion and a second portion, the second pictogram answer has a first portion and a second portion, the first portion of the first pictogram answer substantially corresponding in shape to the first portion of the second pictogram answer and being unrelated to human anatomy, the second portion of the first pictogram answer differing in shape to the second portion of the second pictogram answer.

5. The method of claim 1, wherein the user selection of the first pictogram answer for the first question is received at a first time, and the user selection of the pictogram answer for the second question is received at a second time, the method further comprising:
sending, after the first time and before the second time, a signal representing a first score based on the user selection of the first pictogram answer for the first question; and
sending, after the first time and the second time, a signal representing a second score based on the user selection of the pictogram answer for the second question, the second score being higher than the first score based on having received an additional pictogram answer.

6. The method of claim 1, wherein:
the user selection of the first pictogram answer for the first question defines at least a portion of the health-related user profile at a first time, the user selection of the pictogram answer for the second question defines at least a portion of the health-related user profile at a second time after the first time,
the method further comprising:
sending, after the first time and before the second time, a signal representing at least one of a recommended article indicator or a discussion group indicator based on the health-related user profile at the first time; and
sending, after the first time and the second time, a signal representing at least one of a recommended article indicator or a discussion group indicator based on the health-related user profile at the second time.

7. An apparatus, comprising:
a survey module implemented in at least one of a processor or memory, the survey module configured to:
send a signal representing a first question and a plurality of pictogram answers for the first question to a first user, the plurality of pictogram answers for the first question including a first pictogram answer and a second pictogram answer, the first pictogram answer having a first portion and a second portion, the second pictogram answer having a first portion and a second portion, the first portion of the first pictogram answer substantially corresponding in shape to the first portion of the second pictogram answer and being unrelated to human anatomy, the second portion of the first pictogram answer differing in shape to the second portion of the second pictogram answer;
receive a signal representing a selection of an answer to the first question including a selection of a pictogram answer from the plurality of pictogram answers,
send a signal representing a second question and a plurality of pictogram answers for the second question to the first user, the second question being different from the first question, the plurality of pictogram answers for the second question being different from the plurality of pictogram answers for the first question, the first question and the second question collectively defining at least portion of a health-related survey,
receive a signal representing a selection of an answer to the second question including a selection of a pictogram answer from the plurality of pictogram answers for the second question,
send a signal representing a third question including a plurality of pictogram answers for the third question to a second user,
receive a signal representing a selection of an answer to the third answer including a selection of a pictogram answer from the plurality of pictogram answers for the third question, and
send a signal representing a fourth question and a plurality of pictogram answers for the fourth question to the second user;
a database operatively coupled to the survey module, the database configured to:
store a health-related user profile for the first user based on the answer to the first question and the answer to the second question, and
store a health-related user profile for the second user based on the answer to the third question; and
a reminder module configured to automatically send a signal to the second user based on the health-related user profile of the first user being based on a first number of answers.

8. The apparatus of claim 7, wherein:
the survey module is configured to receive the signal representing the selection of the answer to the first question at a first time, and the survey module is configured to receive the signal representing the selection of the answer to the second question at the second time after the first time, and
the survey module configured to select, after the first time and before the second time, the second question from a plurality of questions based on the answer to the first question.

9. The apparatus of claim 7, wherein:
the survey module is configured to receive the signal representing the selection of the answer to the first question at a first time, the survey module is configured to receive the signal representing the selection of the answer to the second question at the second time after the first time, the apparatus further comprising:
a reward module operably coupled to the database module, the reward module configured to:
cause a first reward to be issued to the first user based on the health-related user profile for the first user being based on a first number of answers,
cause a second reward to be issued to the second user based on the health-related user profile for the second user being based on a second number of answers, the second reward being lesser than the first reward based on the second number being less than the first number,
send, after the first time and before the second time, a signal representing a score based on the answer to the first question, and
send, after the first time and the second time, a signal representing a score based on the selection of the answer to the second question, the score associated with the second question being higher than the score associated with the first question based on the first user having selected an answer to an additional question.

10. The apparatus of claim 7, wherein the survey module is configured to receive the signal representing the selection of the answer to the first question at a first time, the answer to the first question defines at least a portion of the health-related user profile for the first user at the first time, the survey module is configured to receive the signal representing the selection of the answer to the second question at a second time, the answer to the second question defines at least a portion of the health-related user profile for the first user at the second time after the first time,
the apparatus further comprising:
a recommendation module operatively coupled to the survey module, the recommendation module configured to send, after the first time and before the second time, a signal representing at least one of a recommended article indicator or a discussion group indicator based on the health-related profile for the first user at the first time,
the recommendation module configured to send, after the first time and the second time, a signal representing at least one of a recommended article indicator or a discussion group indicator based on the health-related profile for the first user at the second time.

11. The apparatus of claim 7, wherein the plurality of pictogram answers for the first question includes a first pictogram answer having a size and a second pictogram answer having a size larger than the size of the first pictogram answer, the size of the first pictogram answer being associated with a numerical value, the size of the second pictogram answer being associated with a numerical value larger than the numerical value associated with the first pictogram answer.

12. The apparatus of claim 7, wherein the plurality of pictogram answers for the first question includes a first pictogram answer having a directional indicator and a second pictogram answer having a directional indicator different from the directional indicator of the first pictogram answer, the directional indicator of the first pictogram answer being associated with a value, the directional indicator of the second pictogram answer being associated with a value different from the value associated with the first pictogram answer.

* * * * *